United States Patent [19]
Fedij et al.

[11] Patent Number: 5,466,828
[45] Date of Patent: Nov. 14, 1995

[54] CHIRAL 3-CYANO-1-SUBSTITUTED-PYRROLIDINES

[75] Inventors: Victor Fedij, Holland, Mich.; Mark J. Suto, San Diego, Calif.; James N. Wemple; James R. Zeller, both of Holland, Mich.

[73] Assignee: Warner-Lambert Company, Morris Plains, N.J.

[21] Appl. No.: 238,404

[22] Filed: May 5, 1994

Related U.S. Application Data

[62] Division of Ser. No. 88,464, Jul. 7, 1993, Pat. No. 5,347,017.

[51] Int. Cl.$^6$ .................. C07D 207/46; C07D 207/09
[52] U.S. Cl. ..................... 548/566; 548/542; 548/557
[58] Field of Search ........................ 548/567, 557, 548/542, 566

[56] References Cited

U.S. PATENT DOCUMENTS

| | | | |
|---|---|---|---|
| 3,318,908 | 5/1967 | Swidinsky | 548/566 |
| 4,550,103 | 10/1985 | Mich et al. | 514/210 |
| 4,550,104 | 10/1985 | Mich et al. | 514/210 |
| 5,072,001 | 12/1991 | Hagen et al. | 548/572 |
| 5,097,032 | 3/1992 | Domagala et al. | 546/156 |
| 5,157,128 | 10/1992 | Hagen et al. | 548/567 |
| 5,198,449 | 3/1993 | Shanklin, Jr. | 514/317 |
| 5,281,612 | 1/1994 | Domagala et al. | 514/300 |

OTHER PUBLICATIONS

Syn. Commun., 13, 1117 (1983).
J. Org. Chem, 57, 4521 (1992).
J. Med. Chem. 37, Hagen et al., pp. 733–738 (1994).

Primary Examiner—Jacqueline Haley
Attorney, Agent, or Firm—Charles W. Ashbrook

[57] ABSTRACT

Chiral 3-cyanopyrrolidines of the following formula are disclosed, wherein R' is as defined herein. The compounds are useful as intermediates for naphthyridine and quinoline antibiotics.

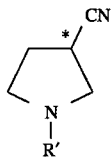

2 Claims, No Drawings

CHIRAL 3-CYANO-1-SUBSTITUTED-PYRROLIDINES

This is a divisional of U.S. application Ser. No. 08/088,464 filed Jul. 7, 1993, now U.S. Pat. No. 5,347,017.

BACKGROUND OF THE INVENTION

Chiral 3-(1-amino-1,1-bisalkylmethyl)- 1-substituted-pyrrolidines are key intermediates in the synthesis of naphthyridine and quinoline antibacterial agents. Such antibacterial agents have been described, for example, in U.S. Pat. Nos. 5,072,001 and related 5,157,128 for which references are incorporated herein.

In the above mentioned patents, there is a description of the process for the preparation of 3-(1-amino-1,1-bisalkylmethyl)-1-substituted-pyrrolidines. For example, 3-(1-amino-1,1-methylethyl)-1-substituted-pyrrolidines are described as being prepared by a 10-step process from dimethyl itaconate and (S)-1-phenethylamine and include several chromatographic procedures to purify intermediates in the overall synthesis.

The object of the present invention is to provide an alternative and improved economical and high yield method for converting inexpensive L-malic acid or its opposite configuration D-malic acid into chiral 3-(1-amino-1,1-bisalkylmethyl)-1-substituted-pyrrolidines, and, in particular, the L-malic acid into (R)-3-(1-amino-1-methylethyl)-1-substituted-pyrrolidines in six steps.

The new method is actually a 3-step process from the readily available starting materials, the chiral 1-substituted-3-pyrrolidinols. Such economical methods are described in European Patent Application Number 452,143. In particular, (S)-1-benzyl-3-pyrrolidinol as a starting material may be prepared in a high yield form L-malic acid in two steps as described by M. M. Bower Nemia, J. Lee, M. M. Joullie, Syn. Commun., 13, 1117 (1983).

Thus, the object of the present invention is also to provide a simple 3-step process for the preparation of chiral 3-(1-amino-1,1-bisalkylmethyl)-1-substituted-pyrrolidines by first converting the alcohol function of a chiral 1-substituted-3-pyrrolidinol to its mesylate or tosylate derivative. Secondly, displacing with cyanide the tosylate or mesylate group resulting in a chiral compound with inverted configuration, and then dialkylating the cyano group with an alkyl carbanion reagent to give the desired chiral pyrrolidine intermediate without racemization and with retention of configuration. The use of alkyl cerium dichloride reagents such as methyl cerium dichloride has been reported to add to non-chiral and racemic nitriles to give corresponding primary amines, J. E. Ciganek, J. Org. Chem., 57, 4521 (1992). The present invention is the first example of addition of an alkylcarbanion to a chiral nitrile, in which the chiral center is located α to the activating nitrile group, to give an optically active tertiary amine with retention of optical purity at the α-carbon site.

SUMMARY OF THE INVENTION

Accordingly, the present invention includes a process for the preparation of compound of Formula I

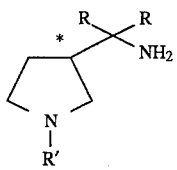

wherein * denotes an asymmetric carbon atom having the R or S configuration; R' is benzyl, p-methoxybenzyl, α-methylbenzyl and its individual optical isomers, methoxy, ethoxy, or dimethylamino, and R is alkyl of 1 to 3 carbon atoms; which comprises:

(1) reacting a chiral 1-R'-pyrrolidinol with an alkane or arylsulfonyl halide in the presence of a suitable base in an aprotic solvent;

(2) converting the chiral 1-R'-3-pyrrolidinol-sulfonyl ester to the corresponding chiral 1-R'- 3-cyanopyrrolidine with inversion of configuration by reaction of the sulfonate ester with a cyanide reagent in a suitable aprotic solvent, and (3) treating the resulting chiral 1-R'-3-cyanopyrrolidine with excess alkyl lithium in the presence of a Lewis acid and an aprotic solvent.

A second aspect of the present invention includes a process for preparing a compound of the Formula I

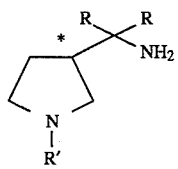

wherein * denotes an asymmetric carbon atom having the R or S configuration; R' is benzyl, p-methoxybenzyl, α-methylbenzyl and its individual optical isomers, methoxy, ethoxy, or dimethylamino, and R is alkyl of 1 to 3 carbon atoms; which comprises:

(1) reacting a 1-R'-3-pyrrolidinolsulfonate ester with a cyanide reagent in a suitable aprotic solvent, and (2) reacting a resulting chiral 1-R'-3-cyano-pyrrolidine with excess alkyl lithium in the presence of a Lewis acid in an aprotic solvent.

A third aspect of the present invention is the process for preparing a compound of the Formula I

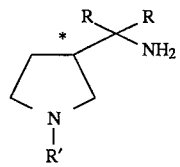

wherein the * denotes an asymmetric carbon atom having the R or S configuration; R' is benzyl, p-methoxybenzyl, α-methylbenzyl and its individual optical isomers, methoxy, ethoxy or dimethylamino, and R is alkyl of 1 to 3 carbon atoms; which comprises:

reacting a chiral 1-R'-3-cyanopyrrolidine with excess alkyl lithium in the presence of a Lewis acid in an aprotic solvent.

A fourth aspect of the present invention are the novel chiral 1-R'-3-cyanopyrrolidine intermediates wherein R' is benzyl, p-methoxybenzyl, methoxy, ethoxy, or dimethylamino.

Finally, a fifth aspect of the present invention are the novel and subsequently prepared chiral teriarybutoxycarbonyl (t-Boc) blocked amino compounds of Formula I wherein R' is benzyl, p-methoxybenzyl, methoxy, ethoxy, or dimethylamino.

The synthesis of the antibacterial agents described in U.S. Pat. Nos. 5,072,001 and 5,157,128 are prepared by first removing the R' group of the chiral t-Boc compounds of Formula I and coupling the resulting chiral pyrrolidine products with the required quinolone or naphthyridone precursor.

DETAILED DESCRIPTION

The term "alkyl" or "alkyl of 1 to 3 carbon atoms" shown in the Formula I as R includes methyl, ethyl, n-propyl, or isopropyl; especially preferred is methyl.

Substituent R' includes benzyl, p-methoxybenzyl, α-methylbenzyl and its optical active isomers, methoxy, ethoxy, or dimethylamino.

An alkane sulfonyl chloride includes, for example, methanesulfonyl chloride, ethanesulfonyl chloride or bromide, or other related alkane sulfonyl halides where alkyl is 1 to 7 carbon atoms and the halide is selected from chlorine, bromine, or iodine.

Arylsulfonyl halide is preferably toluenesulfonyl chloride but also includes benzenesulfonyl chloride or other related arylsulfonyl chlorides where the benzene group may be substituted by other known substituents, for example, halogen, especially chlorine such as p-chlorobenzenesulfonyl halide.

The base used in the conversion of the pyrrolidinol to the corresponding sulfonate ester is an organic nitrogen base. Particularly useful is triethylamine, diazabicycloundecene (DBU), pyridine, quinuclidine, diisopropylethylamine, and the like.

An aprotic solvent may be selected from toluene, methylene chloride, chlorobenzene, tetrahydrofuran, methyl tert-butylether as preferred solvents in the conversion of the pyrridinol to the sulfonate ester.

The chiral cyanopyrrolidine is prepared by reacting the above sulfonate ester with a cyanide reagent. The cyanide reagent may be a cyanide salt, such as an alkali metal cyanide, e.g., sodium or potassium cyanide, in the presence of a phase transfer catalyst or preferably employing the phase transfer catalyst as a reagent per se.

A phase transfer catalyst or reagent is used in the reaction comprising the conversion of the pyrrolidine sulfonate ester to the 1-R'-3-cyanopyrrolidine. Such phase transfer catalyst or reagent allows in some cases the use of water as a cosolvent with the aprotic solvent. The phase transfer catalyst or reagent may be selected preferably from tetrabutylammonium hydrogen sulfate, tetrabutylammonium cyanide, cetylpyridinium cyanide, Aliquat® 336 (tricaprylmethyl-ammonium chloride from Aldrich Chemical Co.) or the corresponding tricaprylmethylammonium cyanide, tetrabutylphosphonium cyanide, and trioctylpropyl-ammonium cyanide.

In the conversion of the sulfonate ester to the cyanopyrrolidine, the preferred aprotic solvent may be selected from dimethylformamide, dimethylsulfoxide, acetonitrile, tetrahydrofuran, N-methylpyrrolidone, chlorobenzene, toluene, sulfolane, or other related aprotic solvents.

In the third reaction which involves the conversion of the 3-cyanopyrrolidine to the dialkylated chiral final product of Formula I, the aprotic solvents preferred are selected from tetrahydrofuran, diethyl ether, di-n-butyl ether, methyl tert- butyl ether, 1,2-dimethoxyethane, or other related aprotic solvents.

In the conversion of the 1-R'-3-cyanopyrrolidine, to the compound of the Formula I, the reaction is carried out in the presence of a Lewis acid. The preferred Lewis acid is cerium chloride. The preferred mode is to mix the Lewis acid with the alkyl lithium prior to reacting it with the 1-R'-3-cyanopyrrolidine.

In the conversion of the pyrrolidinol to the mesylate or tosylate ester, the reaction is carried out at temperatures below to about room temperature, e.g., −10° to 35° C. The subsequent step is carried out at room or elevated temperatures, e.g., from 25° to 100° C. The final reaction which involves the dialkylation of the chiral 3-cyanopyrrolidine to the compound of Formula I, can take place at below room temperature and preferably from −10° to 100° C.

The following is an illustration of the most preferred mode for the process of the present invention. The process is carried out using methanesulfonyloxy as the leaving group in intermediate 1, benzyl as the substituent (R') at the 1 position and methyl lithium as the source of the carbanion nucleophile, thus producing 3 wherein R is to methyl. The phase transfer reagent is tetrabutyl-ammonium cyanide and the Lewis acid is cerium (III) chloride.

Reaction I:

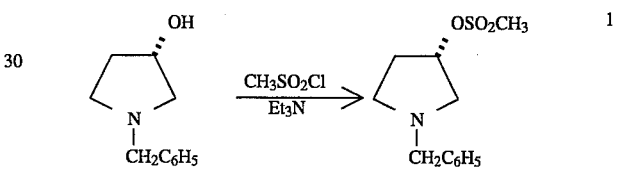

Reaction II:

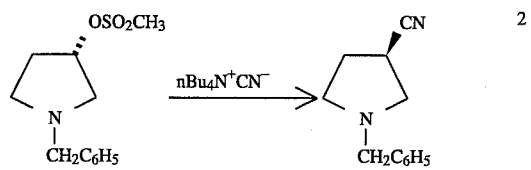

Reaction III:

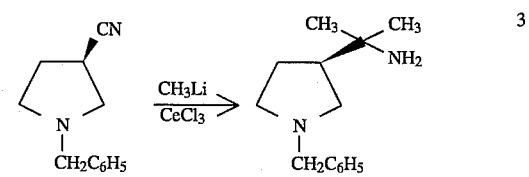

The following examples are illustrative of the present invention.

EXAMPLE 1

(S)-1-Benzyl-3-mesyloxypyrrolidine (S)-1-Benzyl-3-hydroxypyrrolidine (1003.5 g, 5.66 mol) was dissolved in toluene (12 L) and the solution stirred and cooled to 0°–5° C. Triethylamine (680 g, 6.67 mol) was added followed by methanesulfonyl chloride (760 g, 6.63 mol) over a 4 hour period. A slurry formed after 30 minutes. The mixture was allowed to stir an additional 1.5 hours and 7% sodium bicarbonate (12 L) was added to the reaction mixture and the organic layer separated. The aqueous layer was extracted with toluene (4 L and 2 L) and the combined organic layers washed with saturated sodium bicarbonate (3×6 L), dried over MgSO$_4$ and concentrated under reduced pressure to give (S)-1-benzyl-3-mesyloxypyrrolidine as a yellow oil (1.41 kg, 98%):

$^1$HNMR (CDCl$_3$, 200 MHz): δ 2.0–2.6 (m, 4H), 2.85 (d, 2H, J=5), 2.97 (s, 3H), 3.65 (AB, 2H, J=3), 5.20 (m, 1H), 7.3 (m, 5H).

EXAMPLE 2

(R)-1-Benzyl-3-cyanopyrrolidine (S)-1-Benzyl-3-mesyloxypyrrolidine (264.3 g, 1.03 mol) was dissolved in acetonitrile (170 mL) and tetrabutylammonium cyanide (556 g, 2.07 mol) was added. The resulting mixture was heated at 65° C. for 2 days and then cooled to room temperature and saturated NaHCO$_3$ (500 mL) added. The organic layer was separated and the aqueous layer extracted with toluene (600 mL and 400 mL). The combined organic layers were washed with water (4×500 mL) and concentrated under reduced pressure to give (R)-1-benzyl-3-cyanopyrrolidine as a brown oil (165 g, 85.6%): IR: 2239 cm$^{-1}$; VPC: 97.0%;

$^1$HNMR (CDCl$_3$, 200 MHz): δ 2.0–2.4 (m, 2H), 2.6–2.8 (m, 3H), 2.85–3.10 (m, 2H), 3.65 (s, 2H), 7.3 (m, 5H).

EXAMPLE 3

(R)-3-(1-Amino-1-methylethyl)-1-benzylpyrrolidine

Cerium (III) chloride heptahydrate (316 g, 848 mmol) was dried under vacuum at 150°–170° C. for 7 hours. The dry salt was treated with dry THF (2.5 L) and stirred and sonicated for 3.5 hours. The resulting mixture was cooled to −70° C. and methyl lithium (1.0M in diethyl ether stabilized by LiBr, 800 mL, 800 mmol) was added. A solution of (R)-1-benzyl-3-cyanopyrrolidine (49.4 g, 265 mmol) in THF (100 mL) was added. After 3 hours the reaction is quenched with 28% NH$_4$OH (125 mL) and then warmed to room temperature. Methylene chloride (1 L) was added to the resulting slurry and the solids removed by filtration. The filtrate was concentrated under reduced pressure and the residue dissolved in a solution of glacial acetic acid (30 g) and water (1.6 L). The solution was washed with CH$_2$Cl$_2$ (2×500 mL), neutralized with 28% NH$_4$OH (100 mL), and the product extracted with CH$_2$Cl$_2$ (2×500 mL). The combined extracts were dried over MgSO$_4$ and concentrated under reduced pressure to give (R)-3-(1-amino-1-methylethyl)pyrrolidine as a yellow oil (40.3 g, 70%): VPC: 97.0%; [α]$_D$(MeOH, 1.1%)= −9.5° C.;

$^1$HNMR (CDCl$_3$, 200 MHZ): δ 1.05 (s, 6H), 1.4–1.95 (m, 4H), 2.15–2.6 (m, 3H), 2.65–2.8 (m, 2H), 3.5–3.68 (AB, 2H, J=5), 7.26–7.32 (m, 5H).

EXAMPLE 4

(R)-3-[1-(tert-Butoxycarbonylamino)-1-methylethyl]-1-benzylpyrrolidine (R)-3-(1-Amino-1-methylethyl)-1-benzylpyrrolidine (36.3 g, 166 mmol), triethylamine (25.8 g, 255 mmol), and di-tert-butyl dicarbonate (36.5 g, 166 mmol) were dissolved in methylene chloride (500 mL) and the solution stirred overnight at ambient temperature. Water (100 mL) was added and the organic layer separated, washed with water (100 mL) and dried over MgSO$_4$, and concentrated under reduced pressure to give (R)-3-[1-(tert-butoxycarbonylamino)-1-methylethyl]- 1-benzylpyrrolidine as a yellow oil (44.2 g, 85%): VPC: 95.6%; [α]$_D$(MeOH, 1.0%)=+15.5° C.;

$^1$HNMR (CDCl$_3$, 200 MHz): δ 1.30 (s, 6H), 1.47 (s, 9H), 1.75–1.93 (m, 2H), 2.10–2.23 (m, 3H), 2.75–2.93 (m, 2H), 3.60 (s, 2H), 6.10 (s, 1H), 7.25 (m, 5H).

EXAMPLE 5

(R)-3-[1-(tert-Butoxycarbonylamino)-1-methylethyl]pyrrolidine (R)-3-[1-tert-Butoxycarbonylamino)-1-methylethyl]-1-benzylpyrrolidine (78.5 g, 247 mmol) and 20% palladium on carbon (34% water wet, 10.0 g) was dissolved in methanol (1 L) and the mixture hydrogenated with 50 psig hydrogen at 45° C. for 6 days. An additional increment of 20% palladium on carbon (25% water wet, 5.0 g) was added to the reaction mixture and the hydrogenation continued to complete the reduction. The catalyst was removed by filtration and the filtrate concentrated under reduced pressure to give (R)-3-[ 1-(tert-butoxycarbonylamino)-1-methylethyl] pyrrolidine as a yellow oil (51.3 g, 91%: VPC 94.0%; [α]$_D$(MeOH, 1.1%)=+21.0° C.;

$^1$HNMR (CDCl$_3$, 200 MHz): δ 1.17 (d, 6H, J=3), 1.30 (s, 9H), 1.40–1.55 (m, 1H), 1.6–1.8 (m, 1H), 2.37–2.55 (m, 1H), 2.6–3.1 (m, 5H), 4.8 (s, 1H).

The product of Example 5 may be coupled as described in U.S. Pat. Nos. 5,072,001 and 5,157,128 with a corresponding naphthyridine or quinoline having a leaving group at the 7-position to form the chiral 7-[3-(1-amino-1,1-bisalkylmethyl)- 1-pyrrolidinyl]naphthyridine- or quinoline-3-carboxylic acids as antibacterial agents.

EXAMPLE 6

In a similar manner, the corresponding (S) isomer of 3-(1-amino-1-methylethyl)-1-benzylpyrrolidine may be prepared starting from (R)-1-benzyl-3-pyrrolidinol.

(R)-1-Benzyl-3-mesyloxypyrrolidine (R)-1-Benzyl-3-hydroxypyrrolidine (3.9 g, 22 mmol) was dissolved in toluene (100 mL) and the solution stirred and cooled to 0°–5° C. Triethylamine (2.66 g, 26.2 mmol) was added followed by methanesulfonyl chloride (3.0 g, 26 mmol). A slurry formed after 30 minutes. The mixture was allowed to warm to room temperature and stirred overnight. Water (100 mL) was added to the reaction mixture and the organic layer separated and washed with water (100 mL) and concentrated under reduced pressure to give (R)-1-benzyl-3-mesyloxypyrrolidine (5.7 g) as a yellow oil:

$^1$HNMR (CDCl$_3$), 60 MHz): δ 1.9–2.7 (m, 4H), 2.78 (d, 2H, J=15), 2.90 (s, 3H), 3.65 (s, 2H), 4.9–5.3 (m, 1H), 7.28 (s, 5H).

(S)-1-Benzyl-3-cyanopyrrolidine (R)-1-Benzyl-3-mesyloxypyrrolidine (5.0 g, 20 mmol) was dissolved in acetonitrile (6 mL) and tetrabutylammonium cyanide (11.1 g, 41.4 mmol) was added. The mixture was heated at 65° C. for 3 hours and then cooled to room temperature and extracted with ethyl ether (100 mL). The organic layer was washed with saturated NaHCO$_3$ (2×50 mL), dried over MgSO$_4$, and concentrated under reduced pressure to give (S)-1-benzyl-3-cyanopyrrolidine (3.1 g, 85%) as a yellow oil: VPC: 100%;

$^1$HNMR (CDCl$_3$, 60 MHz): δ 1.9–2.4 (m, 2H), 2.5–3.1 (m, 5H), 3.60 (s, 2H), 7.30 (s, 5H).

(S)-3-(1-Amino-1-methylethyl)-1-benzylpyrrolidine

Cerium (III) chloride heptahydrate (8.0 g, 21 mmol) was dried under vacuum at 140°–150° C. for 1.5 hours. The dried salt was cooled to room temperature and treated with dry THF (70 mL) and the mixture stirred for 30 minutes followed by sonication for 1 hour. The resulting reaction mixture was cooled to −70° C. and methyl lithium (1.0M in ethyl ether stabilized by LiBr, 21.5 mL, 21.5 mmol) was added. A solution of (S)-1-benzyl-3-cyanopyrrolidine (1.0 g, 5.4 mmol) in THF (5 mL) was added to the mixture which was then allowed to stir 8 hours. The mixture was treated with concentrated $NH_4OH$ (25 mL) and the resulting solids removed by filtration. The filtrate was extracted with $CH_2Cl_2$ (50 mL). The organic layer was separated and the aqueous layer extracted with $CH_2Cl_2$ (25 mL). The combined organic layers were dried over $MgSO_4$ and concentrated under reduced pressure to an oil which was purified by flash column chromatography utilizing $MeOH/NH_4OH$ (trace) as eluant to obtain (S)-3-(1-amino-1-methylethyl)-1-benzylpyrrolidine (0.62 g, 53%): VPC: 98.5%; $[\alpha]_D$(MeOH, 1.3%)=+11.7° C.;

$^1$HNMR ($CDCl_3$, 60 MHz): δ 1.00 (s, 6H), 1.30 (s, 2H), 1.55–2.87 (m, 7H), 3.60 (s, 2H), 7.40 (s, 5H).

EXAMPLE 7

1-[1-(S)-α-Methylbenzyl]-3-(R)-cyanopyrrolidine

1-[1-(S)-1-α-Methylbenzyl]-3-(S)-hydroxypyrrolidine (3.2 g, 17 mmol) was dissolved in methylene chloride (50 mL) and triethylamine (1.86 g, 18.4 mmol) added. The solution was cooled in an ice bath and treated dropwise with methanesulfonyl chloride (2.1 g, 18.4 mmol). The resulting mixture was allowed to warm to room temperature where it was stirred for 18 hours. Water was added and the organic layer separated and dried. The solution was concentrated and the residue dissolved in acetonitrile (10 mL). Tetra-n-butylammonium cyanide (9.0 g) was added and the resulting mixture heated at reflux for 3 hours. The mixture was cooled and partitioned between water and ether. The ether layer was separated and washed with saturated sodium bicarbonate, dried, and concentrated. The residue was purified by chromatography on silica gel eluting with ethyl acetate/hexanes (50:50) to give 1-[1-(S)-α-methylbenzyl]-3-(R)-cyanopyrrolidine (1.45 g, 44%):

$^1$HNMR ($CDCl_3$: δ 1.37 (d, 3H), 2.18 (m, 2H), 2.44–2.99 (m, 5H), 3.27 (q, 1H), 7.29 (s, 5H); MS (m+1)=200.

EXAMPLE 8

(R)-3-[1(tert-Butoxycarbonylamino)-1-methylethyl]-1-[1-(S)-α-methylbenzyl]pyrrolidine Cerium (III) chloride heptahydrate (7.21 g, 19.3 mmol) was dried under vacuum at 140°–150° C. for 1.5 to 2 hours. The dried salt was cooled to room temperature and the flask cooled in an ice bath. The dried salt was treated with dry THF (38 mL) and the mixture stirred for 2 hours followed by sonication for 0.5 hour. The mixture was cooled to −78° C. and methyl lithium (1.5M in ethyl ether stabilized by LiBr, 12.5 mL, 19 mmol) was added. The resulting brown suspension was stirred for 30 minutes and a solution of 1-[1-(S)-α-methylbenzyl]-3-(R)-cyanopyrrolidine (1.25 g, 6.25 mmol) in THF (15 mL) was added to the mixture while maintaining the reaction temperature below −60° C. The mixture was allowed to stir 2 hours and then treated with concentrated $NH_4OH$ (20 mL) at −45° C. After warming to room temperature, the solids were removed by filtration through celite and the residue washed with methylene chloride. From the combined filtrates, the aqueous layer was separated and the organic layer concentrated. The residue dissolved in toluene (20 mL) and 3% aqueous phosphoric acid added. After stirring for 30 minutes, the organic layer was separated and the aqueous layer made basic with concentrated $NH_4OH$ and this extracted with $CH_2Cl_2$. The methylene chloride extract was dried and concentrated to provide 1.3 g of 3-(R)-(1-amino- 1-methylethyl)-1-[1-(S)-α-methylbenzyl]pyrrolidine. This was dissolved in methylene chloride (50 mL) and triethylamine (0.62 g, 6.2 mmol) followed by di-tert-butyl dicarbonate (1.3 g, 6.0 mmol) were added and the mixture stirred overnight. Water was added and the organic layer separated and dried and concentrated to give (R)-3-[1-(tert-butoxycarbonylamino)- 1-methylethyl]-1-[1-(S)-α-methylbenzyl]pyrrolidine:

$^1$HNMR ($CDCl_3$: δ 1.28 (s, 3H), 1.34 (m, 6H), 1.46 (s, 9H), 1.61–1.81 (m, 2H), 2.01–2.27 (m, 3H), 2.57 (m, 1H), 2.98 (d, 1H), 3.13 (q, 1H), 6.4 (bs, 1H), 7.31 (m, 5H); MS (m+1)=333.

EXAMPLE 9

(R)-3-[1-(tert-Butoxycarbonylamino)-2-methylethyl]-pyrrolidine (R)-3-[1-(tert-Butoxycarbonylamino)-1-methylethyl]-1-[1-(S)-α-methylbenzyl]pyrrolidine (1.45 g, 4.4 mmol) and 20% palladium on carbon (0.3 g) was dissolved in methanol (100 mL) and the mixture hydrogenated for 18 hours. The catalyst was removed by filtration and the filtrate concentrated to give (R)-3-[1-(tert-butoxycarbonylamino)- 1-methylethyl]pyrrolidine (0.9 g, 92%); $[\alpha]_D$(MeOH, 0.6%)=+17.6° C.

We claim:

1. A chiral compound of the formula

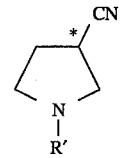

in which * denotes an asymmetric carbon atom having the R configuration, and R' is p-methoxybenzyl, methoxy, ethoxy, or dimethylamino.

2. A compound of claim 1, wherein R' is p-methoxybenzyl.

* * * * *